US00PP23888P2

(12) United States Plant Patent
Oostveen

(10) Patent No.: US PP23,888 P2
(45) Date of Patent: Sep. 10, 2013

(54) ***HIBISCUS* PLANT NAMED 'OAK SOFT PINK'**

(50) Latin Name: *Hibiscus moscheutos*
Varietal Denomination: Oak Soft Pink

(75) Inventor: Cornelis A. Oostveen, De Kwakel (NL)

(73) Assignee: De Zonnebloem Breeding B.V., De Kwakel (NL)

( * ) Notice: Subject to any disclaimer, the term of this patent is extended or adjusted under 35 U.S.C. 154(b) by 59 days.

(21) Appl. No.: 13/373,741

(22) Filed: Nov. 28, 2011

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — C. A. Whealy

(57) ABSTRACT

A new and distinct cultivar of *Hibiscus* plant named 'Oak Soft Pink', characterized by its upright and somewhat outwardly spreading plant form; oak leaf-shaped leaves; freely flowering habit; large light red purple-colored flowers with dark red-colored centers; and good flower longevity.

2 Drawing Sheets

Botanical designation: *Hibiscus moscheutos*.
Cultivar denomination: 'OAK SOFT PINK'.

BACKGROUND OF THE INVENTION

The present invention relates to a new and distinct cultivar of *Hibiscus* plant, botanically known as *Hibiscus moscheutos* and hereinafter referred to by the name 'Oak Soft Pink'.

The new *Hibiscus* plant is a product of a planned breeding program conducted by the Inventor in De Kwakel, The Netherlands. The objective of the breeding program is to create new *Hibiscus* plants with attractive and large flowers.

The new *Hibiscus* plant originated from a cross-pollination in August, 2009 in De Kwakel, The Netherlands of a proprietary selection of *Hibiscus moscheutos* identified as code number CB10, not patented, as the female, or seed, parent with *Hibiscus moscheutos* 'Extrepink', disclosed in U.S. Plant Pat. No. 23,130, as the male, or pollen, parent. The new *Hibiscus* plant was discovered and selected by the Inventor as a single flowering plant from within the progeny of the stated cross-pollination in a controlled greenhouse environment in De Kwakel, The Netherlands in August, 2010.

Asexual reproduction of the new *Hibiscus* plant by vegetative cuttings in a controlled greenhouse environment in De Kwakel, The Netherlands since September, 2010 has shown that the unique features of this new *Hibiscus* plant are stable and reproduced true to type in successive generations.

SUMMARY OF THE INVENTION

Plants of the new *Hibiscus* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Oak Soft Pink'. These characteristics in combination distinguish 'Oak Soft Pink' as a new and distinct *Hibiscus* plant:

1. Upright and somewhat outwardly spreading plant form.
2. Oak leaf-shaped leaves.

3. Freely flowering habit.
4. Large light red purple-colored flowers with dark red-colored centers.
5. Good flower longevity.

Plants of the new *Hibiscus* can be compared to plants of the female parent selection. Plants of the new *Hibiscus* differ primarily from plants of the female parent selection in the following characteristics:

1. Plants of the new *Hibiscus* are larger than plants of the female parent selection.
2. Plants of the new *Hibiscus* and the female parent selection differ in leaf shape as plants of the female parent selection have cordate-shaped leaves.
3. Plants of the new *Hibiscus* have larger flowers than plants of the female parent selection.
4. Plants of the new *Hibiscus* and the female parent selection differ slightly in flower color.

Plants of the new *Hibiscus* can be compared to plants of the male parent, 'Extrepink'. Plants of the new *Hibiscus* differ primarily from plants of 'Extrepink' in the following characteristics:

1. Plants of the new *Hibiscus* and 'Extrepink' differ in leaf shape as plants of 'Extrepink' have cordate-shaped leaves.
2. Plants of the new *Hibiscus* have lighter-colored flowers than plants of 'Extrepink'.

Plants of the new *Hibiscus* can be compared to plants of *Hibiscus moscheutos* 'Mauvelous', not patented. Plants of the new *Hibiscus* differ primarily from plants of 'Mauvelous' in the following characteristics:

1. Plants of the new *Hibiscus* and 'Mauvelous' differ in leaf shape as plants of 'Mauvelous' have rounded leaves.
2. Plants of the new *Hibiscus* and 'Mauvelous' differ slightly in leaf color.
3. Plants of the new *Hibiscus* and 'Mauvelous' differ slightly in flower color as plants of 'Mauvelous'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of typical flowering plants of 'Oak Soft Pink' grown in a container.

The photograph at the top of the second sheet is a close-up view of a typical flower of 'Oak Soft Pink'.

DETAILED BOTANICAL DESCRIPTION

The aforementioned photographs and following observations, measurements and values describe plants grown during the late summer in five-liter containers in a glass-covered greenhouse in De Kwakel, The Netherlands and under cultural practices which closely approximate commercial *Hibiscus* production. During the production of the plants, day temperatures ranged from 18° C. to 33° C. and night temperatures ranged from 18° C. to 25° C. Plants were 14 weeks old when the photographs and the description were taken. In the description, color references are made to The Royal Horticultural Society Colour Chart, 2007 Edition, except where general terms of ordinary dictionary significance are used.

Botanical classification: *Hibiscus moscheutos* 'Oak Soft Pink'.

Parentage:

*Female, or seed, parent*.—Proprietary selection of *Hibiscus moscheutos* identified as code number CB10, not patented.

*Male or pollen parent*.—*Hibiscus moscheutos* 'Extrepink', disclosed in U.S. Plant Pat. No. 23,130.

Propagation:

*Type*.—By vegetative cuttings.

*Time to initiate roots, summer*.—About seven days at temperatures of 22° C.

*Time to initiate roots, winter*.—About ten days at temperatures of 19° C.

*Time to produce a rooted young plant, summer*.—About three weeks at temperatures of 21° C.

*Time to produce a rooted young plant, winter*.—About four weeks at temperatures of 18° C.

*Root description*.—Medium in thickness, fibrous; white to light brown in color.

*Rooting habit*.—Freely branching; dense.

Plant description:

*Plant form and growth habit*.—Upright and somewhat outwardly spreading plant form, broad inverted triangular plant form; moderately vigorous growth habit.

*Branching habit*.—Moderate branching habit, usually about nine lateral branches develop; pinching enhances lateral branch development.

*Plant height*.—About 70.5 cm.

*Plant diameter* (*area of spread*).—About 78.8 cm.

Lateral branch description:

*Length*.—About 59.7 cm.

*Diameter*.—About 5 mm.

*Internode length*.—About 3.5 cm.

*Strength*.—Moderately strong.

*Texture*.—Smooth, glabrous.

*Color*.—Close to 144A to 144B flushed with close to 152A.

Foliage description:

*Arrangement*.—Alternate, single.

*Length*.—About 13.2 cm.

*Width*.—About 9.9 cm.

*Shape*.—Ovate, lobed; oak leaf-shaped.

*Apex*.—Long apiculate.

*Base*.—Cordate.

*Margin*.—Bluntly dentate.

*Texture, upper and lower surfaces*.—Smooth, glabrous.

*Venation pattern*.—Pinnate.

*Color*.—Developing leaves, upper surface: Close to 137B. Developing leaves, lower surface: Close to 138B. Fully expanded leaves, upper surface: Close to N137C; venation, close to 144A. Fully expanded leaves, lower surface: Between 138B and 147B; venation, close to 145B.

*Petiole*.—Length: About 7.7 cm. Diameter: About 3 mm. Texture, upper and lower surfaces: Smooth, glabrous. Color, upper and lower surfaces: Close to 144A.

Flower description:

*Flower arrangement*.—Large rotate flowers arranged singly at terminal leaf axils; freely flowering habit with about 50 flowers developing per plant; flowers face mostly outwardly to slightly upright.

*Fragrance*.—None detected.

*Flower longevity*.—Good flower longevity, flowers last for about four days; flowers not persistent.

*Natural flowering season*.—Plants flower from late summer into the autumn in The Netherlands; plants begin flowering about ten weeks after planting.

*Flower diameter*.—About 20.3 cm.

*Flower length* (*height*).—About 4.6 cm.

*Flower bud*.—Rate of opening: Flowers buds open in about four days. Length: About 4.2 cm. Diameter: About 3.1 cm. Shape: Ovate. Color: Close to 143B to 143C; towards the apex, close to between 63A and 70D.

*Petals*.—Arrangement: Corolla consists of five petals in a single whorl; petals imbricate. Length: About 9.9 cm. Width: About 10.2 cm. Shape: Reniform to nearly orbicular. Apex: Rounded. Base: Attenuate. Margin: Entire. Texture, upper and lower surfaces: Smooth, glabrous; rugose. Color: When opening and fully opened, upper surface: Close to 73B; towards the base, close to 75B to 75C; base, close to 46A to 46C; venation, close to 68A; color becoming closer to 73A with development. When opening and fully opened, lower surface: Close to 65B; towards the apex, close to 65A; towards the base, close to 155B.

*Sepals*.—Appearance: Five sepals fused into a tubular star-shaped calyx. Length: About 3.6 cm. Width: About 2.1 cm. Shape: Ovate. Apex: Abruptly acute. Margin: Entire. Texture, upper and lower surfaces: Smooth, glabrous. Color, immature and mature, upper surface: Close to 143C. Color, immature and mature, lower surface: Close to 143B to 143C.

*Peduncles*.—Length: About 7.8 cm. Diameter: About 2 mm. Angle: About 30° from the lateral branch axis. Strength: Moderately strong. Texture: Smooth, glabrous. Color: Close to 144A.

*Reproductive organs*.—Androecium: Stamen number: Numerous, about 150. Filament length: About 4 mm. Filament color: Close to 155A. Anther shape: Orbicular. Anther length: About 2 mm. Anther color: Close to 52B. Amount of pollen: Abundant. Pollen color: Close to 11C to 11D. Gynoecium: Pistil length: About 4.5 cm. Style length: About 4.3 cm. Style color: Close to 155C. Stigma appearance: Five-parted, club-shaped. Stigma color: Close to 160C. Ovary color: Close to 149B.

*Seeds and fruits*.—Seed and fruit development have not been observed on plants of the new *Hibiscus*.

Temperature tolerance: Plants of the new *Hibiscus* have been observed to tolerate high temperatures of about 35° C. and to be hardy to USDA Hardiness Zone 6.

Pathogen & pest resistance: Plants of the new *Hibiscus* have not been observed to be resistant to pathogens and pests common to *Hibiscus*.

It is claimed:

1. A new and distinct *Hibiscus* plant named 'Oak Soft Pink' as illustrated and described.

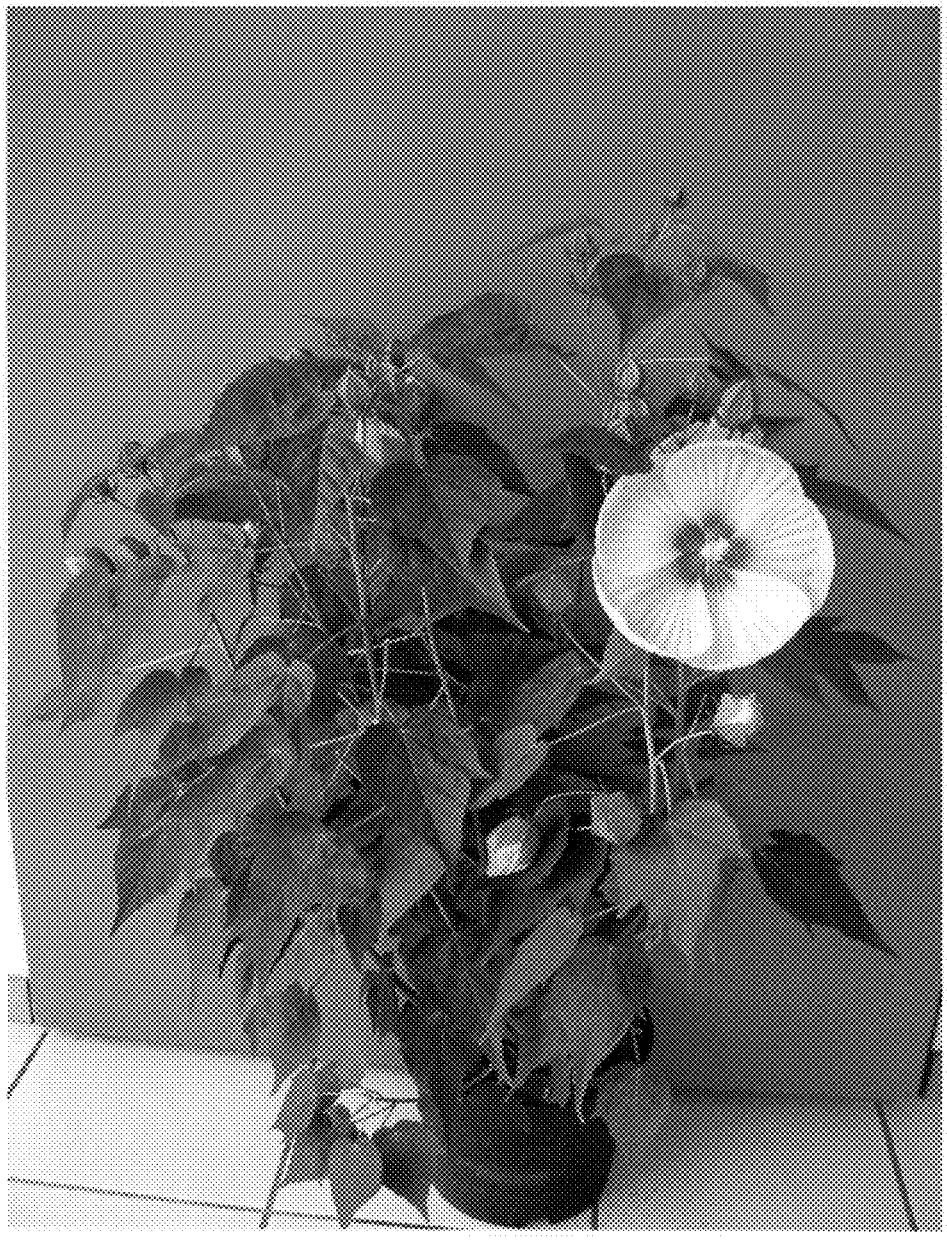

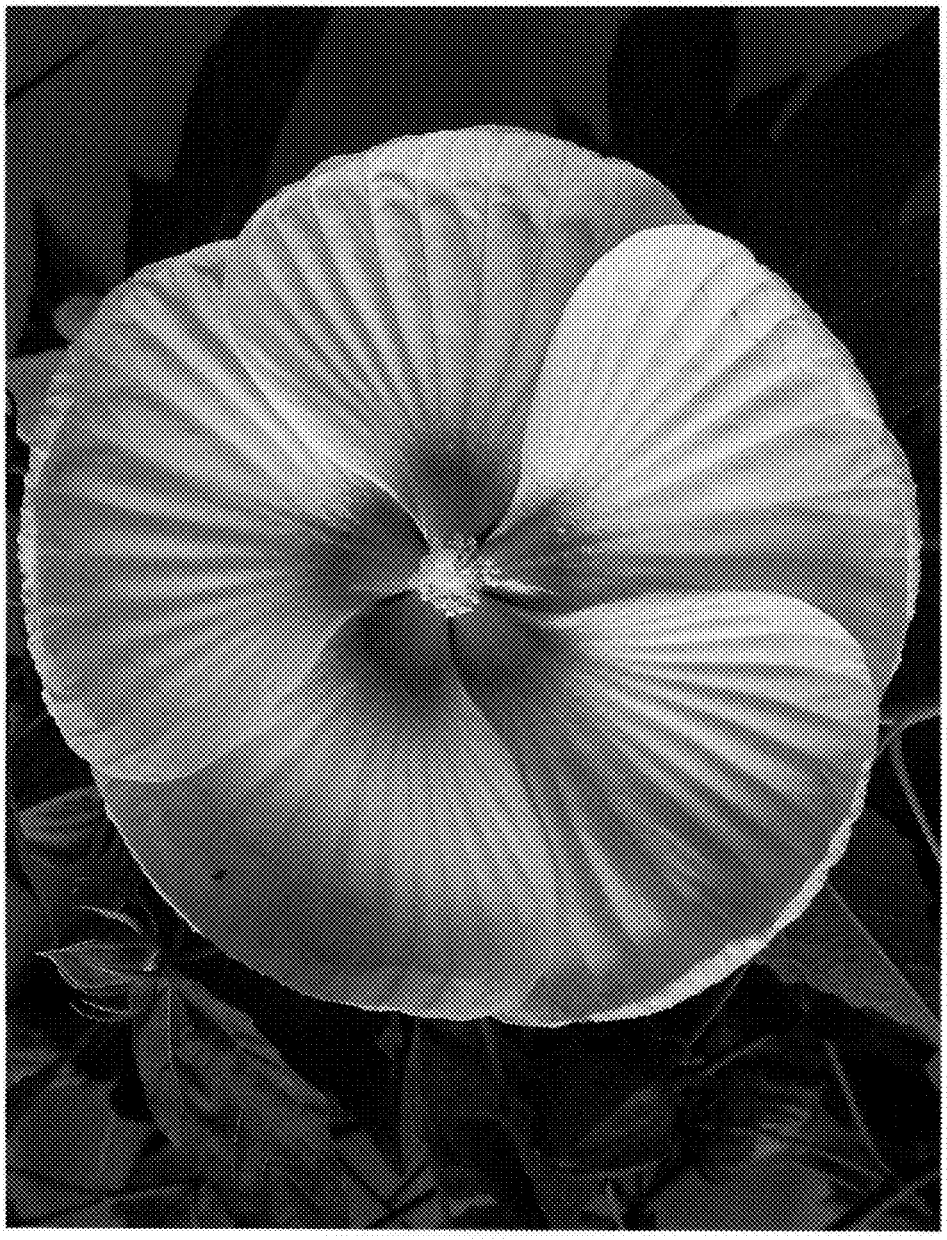

* * * * *